United States Patent [19]

Lang

[11] 3,955,918
[45] May 11, 1976

[54] AZO DERIVATIVES OR PYRIDINE N-OXIDE FOR USE IN HAIR DYE COMPOSITIONS

[75] Inventor: Gerard Lang, Epinay-sur-Seine, France

[73] Assignee: Societe Anonyme dite: L'Oreal, Paris, France

[22] Filed: June 18, 1973

[21] Appl. No.: 370,651

[30] Foreign Application Priority Data
June 19, 1972 France .............................. 72.65539

[52] U.S. Cl. ........................................ 8/10; 8/10.1; 8/41 R; 260/156
[51] Int. Cl.² ........................................... D06P 3/06
[58] Field of Search ................. 260/156; 8/10.1, 10, 8/41 R

[56] References Cited
UNITED STATES PATENTS

| | | | |
|---|---|---|---|
| 3,249,597 | 5/1966 | Dehn, Jr. et al. .................... | 260/156 |
| 3,368,941 | 2/1968 | Boosen .................................. | 8/10.1 |
| 3,386,991 | 6/1968 | Gerber................................. | 260/156 |
| 3,393,190 | 7/1968 | Stright ............................ | 260/156 X |

Primary Examiner—Norman A. Drezin
Assistant Examiner—Vera C. Clarke
Attorney, Agent, or Firm—Cushman, Darby and Cushman

[57] ABSTRACT

Compositions for dyeing human hair contain in an aqueous or hydroalcoholic solution an azo derivative of pyridine N-oxide as a hair dye present in amounts of 0.001 – 1 weight percent of said composition which has a pH ranging from 3 – 9.5.

4 Claims, No Drawings

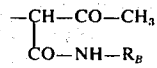

AZO DERIVATIVES OR PYRIDINE N-OXIDE FOR USE IN HAIR DYE COMPOSITIONS

The present invention relates to dye compositions for human hair, characterized by the fact that they include in solution one or more compounds of the formula:

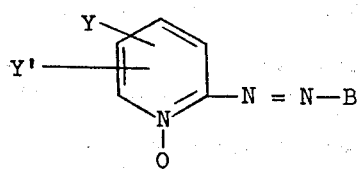

or one or more O-alkyl derivatives of these compounds, of the formula

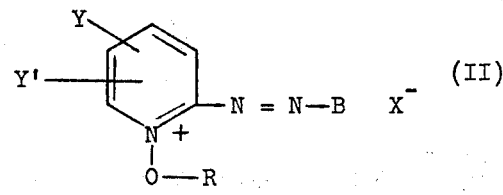

wherein
Y and Y' each represent hydrogen, halogen, lower alkyl having 1–4 carbon atoms, lower alkoxy having 1–4 carbon atoms, nitro or carboxyl;
R represents lower alkyl having 1–4 carbon atoms;
$X^-$ represents an anion such as methylsulfate, iodide or perchlorate,
B represents a member selected from the group consisting of
  a. phenyl substituted in a position selected from the group consisting of ortho and para positions relative to the nitrogen atom of the disazo link, by a member selected from the group consisting of hydroxy and primary, secondary or tertiary amino and optionally carrying one or more further substituents selected from the group consisting of lower alkyl having 1–4 carbon atoms, lower alkoxy having 1–4 carbon atoms, halogen, a primary, secondary or tertiary amino, acetamido, nitro and hydroxy, said phenyl being further optionally condensed with a benzene or heterocyclic ring;
  b. a group of the formula

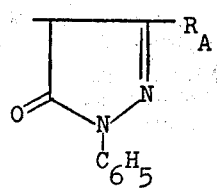

wherein
$R_A$ is selected from the group consisting of methyl and ethyl; and
  c. a group of the formula $$-\underset{\underset{CO-NH-R_B}{|}}{CH}-CO-CH_3$$

wherein
$R_B$ represents a member selected from the group consisting of lower alkyl having 1–4 carbon atoms and phenyl.

The compounds represented by formula I and II above include a certain number of compounds which have been known for use in dyeing synthetic fibers. However these known compounds, until now, have been disclosed as being useful in the dyeing of human hair.

It has now been discovered that these dyes exhibit an excellent affinity for human hair and provide luminous and stable colorations ranging from yellow to blue.

The dyes of formulae I and II exhibit, relative to known disazo dyes for coloring hair, the advantage of being more soluble in water and of providing a significantly wider range of colors, especially since the colorations attainable range from yellow to blue.

The compositions of the present invention are aqueous or hydroalcoholic solutions that can easily be prepared by dissolving in water or in a mixture of water and alcohol, one or more compounds of formulae I or II. The alcohol employed in said compositions is generally present in amounts of about 5–70 percent by weight thereof and is generally ethanol or isopropanol.

The concentration of the compounds of formulae I and II in the dye composition of the present invention can vary widely because of their good affinity for hair. This concentration is generally between about 0.001 – 1 percent by weight of said composition.

The pH of the composition according to the present invention is generally between about 3–9.5 and the pH can be adjusted to the desired value by the addition to said composition of an acid such as orthophosphoric or acetic acid, or of a base such as triethanolamine or ammonia. Obviously, other pH adjusting agents conventionally employed in cosmetic compositions can also be utilized.

The composition of the present invention can also include various conventionally employed cosmetic adjuvants such as wetting agents, dispersing agents, swelling agents, penetrating agents, emolients and perfumes. Further, the composition of the present invention can be packaged under pressure in an aerosol bomb or container with a conventional liquefied aerosol propellant, such as fluorinated hydrocarbon including dichlorodifluoromethane, trichloromonofluoromethane and mixtures thereof.

The compositions of the present invention can also include other direct dyes, such as azo dyes, anthraquinone dyes, nitro dyes of the benzene series, indoanilines, indophenols or indamines.

The composition of the present invention can be utilized to provide a durable dyeing of the hair, in which case it is applied to the hair and left in contact therewith for a period of about 3–30 minutes. This application is followed by rinsing, washing and drying the thus dyed hair.

The compositions of the present invention can also be employed as a rinse lotion which imparts to the hair a light coloration, in which case they are applied to previously washed hair and the application of the same is not followed by a rinsing of the hair.

The compositions of the present invention can also be employed as hair setting lotions which both impart to the hair a light coloration and improve the holding power of the hair set. In this case, the compositions are present in the form of a hydroalcoholic solution containing at least one cosmetic film-forming resin having a molecular weight ranging from about 10,000 to 3,000,000. These compositions are generally applied to previously washed and rinsed wet hair which is then rolled up on curlers and dried.

The cosmetic film-forming resins usufully employed in said hair setting lotions are present therein in amounts of about 1–3 percent by weight of said composition and include for instance, polyvinylpyrrolidone having a molecular weight between 40,000 and 400,000; 70–30%/30–70% vinylpyrrolidone/vinyl acetate copolymers; copolymers of vinyl acetate and an unsaturated carboxylic acid such as crotonic acid (90:10) having a molecular weight ranging from about 20,000–50,000, preferably about 45,000–50,000; copolymers of maleic anhydride and butyl vinyl ether copolymers resulting from the polymerization of vinyl acetate (75–85%), crotonic acid (5–15%) and an acrylic or methacrylic ester (5–15%) or an alkyl vinyl ether (5–15%); copolymers resulting from the copolymerization of vinyl acetate (63–88%), crotonic acid (5–15%) and (a) (5–25%) of a vinyl ester of an acid with a long carbon chain having 10–22 carbon atoms or (b) 5–25% of an allyl or methallyl ester of an acid with a long carbon chain having 10–22 carbon atoms; copolymers resulting from the copolymerization of 65–80% of an ester of an unsaturated alcohol having from 2 to 12 carbon atoms and a carboxylic acid having from 2 to 5 carbon atoms, 7–12% of an unsaturated acid having from 4 to 20 carbon atoms and 10–20% of at least an ester of a saturated alcohol having from 8 to 18 carbon atoms and an unsaturated acid having from 4 to 20 carbon atoms.

The hair setting lotions of the present invention generally contain about 20–70 weight percent low molecular weight alcohol such as ethanol or isopropanol.

Included in the dyes of formulae I and II defined above are a certain number of new compounds which are also a part of the present invention.

Consequently the present invention also has for an object a new industrial product which is a compound of the formula

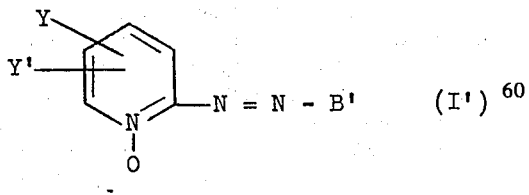

and the O-alkyl derivatives thereof having the formula:

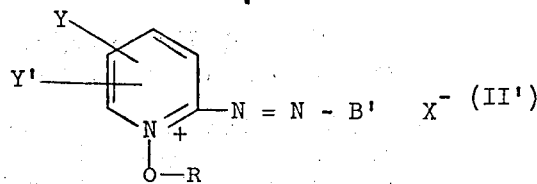

wherein
Y and Y' each independently represent hydrogen, halogen, lower alkyl having 1–4 carbon atoms, lower alkoxy having 1–4 carbon atoms, nitro or carboxy;
R represents lower alkyl having 1–4 carbon atoms,
X⁻ represents an anion such as methylsulfate, iodide or perchlorate,
B' represents a member selected from the group consisting of (1) 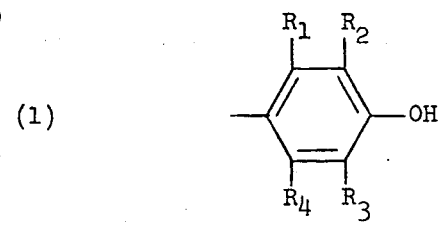

wherein
$R_1$, $R_2$ and $R_3$ each independently represent a member selected from the group consisting of hydrogen and lower alkyl having 1–4 carbon atoms, and
$R_4$ represents a member selected from the group consisting of
i. hydrogen,
ii. lower alkyl having 1–4 carbon atoms, and
iii.

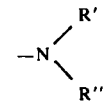

wherein R' is selected from the group consisting of hydrogen and lower alkyl having 1–4 carbon atoms and R'' is selected from the group consisting of hydrogen, lower alkyl having 1–4 carbon atoms, lower alkyl having 1–4 carbon atoms and substituted by a member selected from the group consisting of amine, amide and

where X represents a member selected from the group consisting of oxygen and sulfur and R''' is selected from the group consisting of amino and lower alkyl having 1–4 carbon atoms,
at least one of $R_1$ to $R_4$ being other than hydrogen, and $R_4$ and $R_3$ form together with the benzene nucleus to which they are attached, a naphthalene nucleus or a naphthalene nucleus substituted and capable of including one or more heteroatoms;

(2) 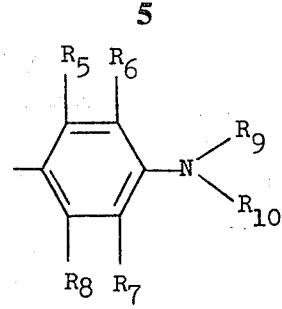

wherein
- $R_5$ and $R_7$ are selected from the group consisting of hydrogen and lower alkyl having 1–4 carbon atoms,
- $R_6$ represents a member selected from the group consisting of hydrogen, lower alkyl having 1–4 carbon atoms and lower alkoxy having 1–4 carbon atoms,
- $R_8$ represents a member selected from the group consisting of hydrogen, nitro or

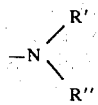

wherein R' and R'' have the meanings given above, or together with $R_7$ form, with the benzene ring to which they are attached a naphthalene ring or a substituted naphthalene ring including one or more heteroatoms,
- $R_9$ represents a member selected from the group consisting of hydrogen, lower alkyl having 1–4 carbon atoms or substituted lower alkyl having 1–4 carbon atoms and
- $R_{10}$ represents a member selected from the group consisting of hydrogen, lower alkyl having 1–4 carbon atoms, phenyl or substituted phenyl; and (3) 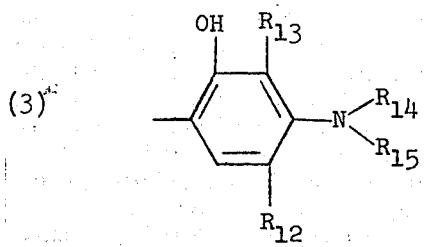

wherein
- $R_{12}$ and $R_{13}$ each independently represent a member selected from the group consisting of hydrogen and lower alkyl having 1–4 carbon atoms, and
- $R_{14}$ and $R_{15}$ each independently represent a member selected from the group consisting of lower alkyl having 1–4 carbon atoms and substituted lower alkyl having 1–4 carbon atoms, or
- $R_{14}$ and $R_{13}$ together with the nitrogen atom to which $R_{14}$ is attached and the carbon atoms to which $R_{13}$ and said nitrogen atom are attached form a heterocycle, saturated or not and capable of including another heteroatom, in which case $R_{12}$ is hydrogen and $R_{15}$ is selected from the group consisting of hydrogen or lower alkyl containing 1–4 carbon atoms; or
- $R_{15}$ and $R_{12}$ together with the nitrogen atom to which $R_{15}$ is attached and the carbon atoms to which $R_{13}$ and said nitrogen atom are attached form a heterocycle, saturated or not, and capable of including another heteroatom, in which case $R_{13}$ is hydrogen and $R_{14}$ is selected from the group consisting of hydrogen, lower alkyl having 1–4 carbon atoms and acyl.

The new compounds of the present invention can be obtained in accordance with the conventional procedures by condensing a diazonium salt of the formula

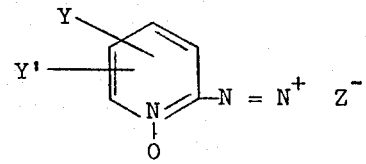

wherein Y and Y' have the meanings given above and $Z^-$ is an anion selected from the group consisting of chloride, orthophosphate and sulfate with a coupler selected from the group consisting of (i) 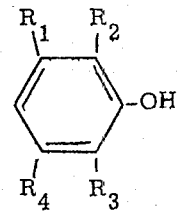

(ii) 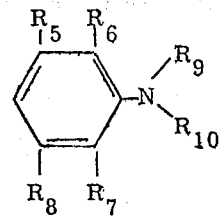

and (iii) 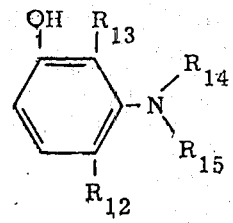

wherein $R_1 - R_{15}$ have the meanings given above.

The new compounds of formula (II') are obtained by reacting an alkylating agent of the formula RX with a compound of the formula (I') wherein R and X have the meanings given above, generally in essentially equimolar amounts, at a temperature ranging from about 20° to 150°C and at atmospheric pressure.

The following examples are given to illustrate the different aspects of the present invention. All parts and percentages are by weight unless otherwise specified.

EXAMPLE 1

Preparation of (2',4'-diamino-5'-methoxy phenyl)-2-azo pyridine N-oxide of the formula

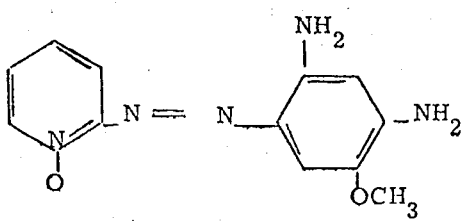

There is slowly added, while maintaining the temperature at 5°C, a solution, cooled to 0°C, of 0.1 mol of 2-N-oxypyridyl diazonium chloride, prepared in accordance with the method of Katrisky, J.C.S. 1957, p. 191, to a solution of 32.5 g of the hydrated sulfate of 2,4-diamino anisole (average molar mass = 325) and of 52 cc of a 40% aqueous solution of sodium acetate in 200 cc of water.

The reaction mixture is left to stand for one hour at ambient temperature, at which time the reaction mixture is neutralized with sodium carbonate. The resulting reaction product is extracted with chloroform. The residue obtained by evaporating to dryness said extract is crystallized in a minimum of water, thus providing red-violet crystals of the above product, having a melting point of 160°C.

EXAMPLE 2

Preparation of (2'-acetamido-3',5'-dimethyl-4'-hydroxy phenyl)-2-azo pyridine N-oxide of the formula

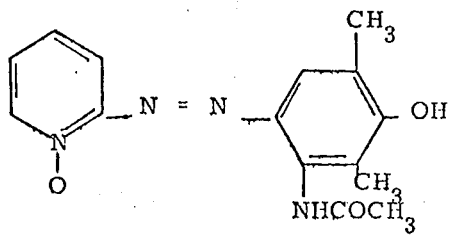

There is slowly added, with agitation and while maintaining the temperature at 5°C, a solution of 0.1 mole of the diazonium salt, prepared in accordance with the method referred to in Example 1, to a solution of 18 g of 3-acetamido-2,6-dimethyl phenol in 12 cc of a 10% sodium hydroxide solution. The reaction mixture is left to stand for one hour at ambient temperature at which time it is acidified to a pH of 4 by the addition thereto of acetic acid. Cooling of the reaction mixture causes precipitation of the above product which is then washed with water, dried on phosphoric anhydride and crystallized in ethyl glycol. The product is in the form of brown crystals having a melting point of 200°C.

Analysis: $C_{15}H_{16}N_4O_3 \cdot 0.5H_2O$ Calculated: C% 59.20; H% 5.50; N% 18.10; Found: C% 59.13; H% 5.74; N% 17.85.

EXAMPLE 3

Preparation of (2'-acetamido-4'-hydroxy-5-methyl phenyl)-2-azo pyridine N-oxide of the formula

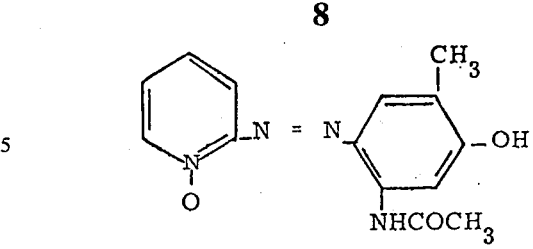

There is slowly added, with agitation and while maintaining the temperature at 5°C, a solution of 0.1 mol of 2-N-oxypyridyl diazonium chloride, prepared in accordance with the method referred to in Example 1, to a solution of 16.6 g of 3-hydroxy-4-methyl acetanilide in 120 cc of a 10% sodium hydroxide solution. The reaction mixture is left to stand for one hour at ambient temperature at which time the same is filtered to remove the precipitate that had formed. The precipitate is washed with a minimum of water and made into a paste with acetic acid, which paste is then washed with sulfonic ether. The resulting product has a melting point with decomposition of 265°C.

Analysis: $C_{14}H_{14}N_4O_3$ Calculated: C% 58.74; H% 4.89; N% 19.57; Found: C% 58.70; H% 5.04; N% 19.56.

EXAMPLE 4

Preparation of (2'-acetamido-4'-dimethylamino phenyl)-2-azo pyridine N-oxide of the formula

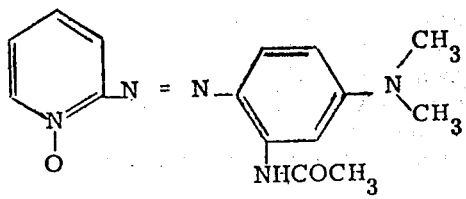

There is slowly added, with agitation and while maintaining the temperature at 5°C, a solution of 0.1 mol of diazonium salt prepared in accordance with the method referred to in Example 1, to a solution of 20 g of 3-dimethylamino acetanilide in 15 cc of acetic acid. The reaction mixture is left to react for 30 minutes at which time there are added 100 cc of a 40% aqueous solution of sodium acetate. The resulting mixture is then agitated for 15 minutes after which the precipitate which has formed is filtered and washed with water. After drying said filtered precipitate and recrystallizing in 50% ethanol, the product exhibited a melting point of 187°C.

Analysis: $C_{15}H_{17}N_5O_2$ Calculated: C% 60.20; H% 5.69; N% 23.41; Found: C% 60.05; H% 5.79; N% 23.26.

EXAMPLE 5

Preparation of (2'-amino-4'-dimethylamino phenyl)-2-azo pyridine N-oxide of the formula

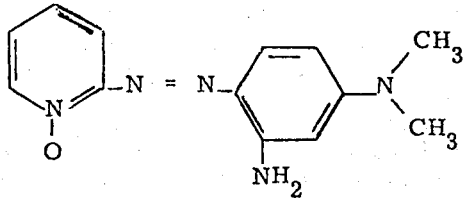

There is added, with agitation and while maintaining the temperature at 5°C, a solution of 0.1 mol of the diazonium salt prepared in accordance with the method referred to in Example 1, to a solution of 13.6 g of N,N-dimethyl metaphenylenedaimine in 12 cc of acetic acid. The reaction mixture is left to stand for one hour at ambient temperature at which time the reaction mixture is neutralized with sodium carbonate. The resulting reaction product is isolated by extraction with chloroform and the concentration of the extract is reduced under pressure. After washing with sulfuric ether and drying the above product exhibits a melting point of 226°C.

EXAMPLE 6

Preparation of (3',5'-dimethyl-4'-hydroxy phenyl-2-azo pyridine N-oxide of the formula

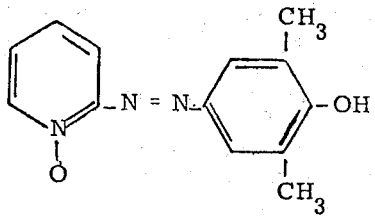

There is slowly added, while maintaining the temperature at 5°C, a solution of 0.1 mol of the diazonium salt prepared in accordance with the method referred to in Example 1, to a solution of 12.2 g of 2,6-dimethyl phenol in 120 cc of a 10% sodium hydroxide solution. The reaction mixture is left to stand for one hour at ambient temperature at which time the reaction mixture is neutralized by the addition thereto of acetic acid. The precipitate which forms is filtered and there is added thereto a minimum of acetone. There is then added an aqueous acetone solution thereto whereupon a precipitate forms which is subsequently filtered. The precipitate thus recovered is recrystallized in methylcellosolve and the above resulting product exhibits a melting point of 179°C.

EXAMPLE 7

Preparation of (4'-dimethylamino-2'-nitro phenyl)-2-azo pyridine N-oxide of the formula

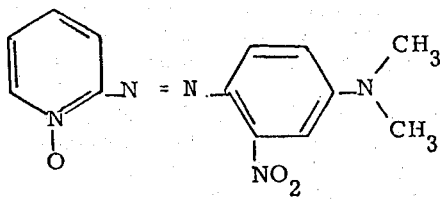

There is slowly added, with agitation and while maintaining the temperature at 5°C, a solution of 0.1 mol of the diazonium salt prepared in accordance with the method referred to in Example 1, to a solution of 17 g of 3-nitro-N,N-dimethyl aniline in 50 cc of 10% HCl. The reaction mixture is left to stand for one hour at ambient temperature, at which time the precipitate which has formed is filtered and washed with cold water. After drying and recrystallizing the same from ethanol, the above product exhibits a melting point of 214°C.

Analysis: $C_{13}H_{13}N_5O_3$ Calculated: N% 24.40; Found: N% 24.13.

EXAMPLE 8

Preparation of (8'-hydroxy-quinoline)-5':2-azo pyridine N-oxide of the formula

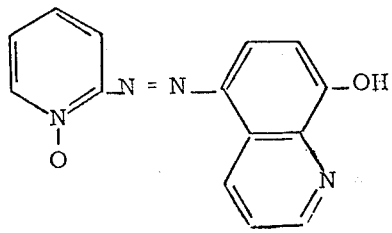

There is slowly added, with agitation and while maintaining the temperature at +5°C, a solution of 0.1 mol of the 2-N-oxypyridyl diazonium chloride prepared in accordance with the method referred to in Example 1, to a solution of 14.5 g of 8hydroxy quinoline in 200 cc of methanol and 40 cc of a 10% solution of sodium hydroxide. The reaction mixture is left to stand for one hour at ambient temperature at which time the precipitate which has formed is filtered therefrom. After having made a paste of the same several times in dilute ammonia and then washed with water, the same is washed twice with 50 cc of a 50% aqueous solution of methanol and then four times with 50 cc of acetone. The thus treated precipitate is then dried and recrystallized in methylcellosolve, the resulting product exhibiting a melting point with decomposition of 260°C.

Analysis: $C_{14}H_{10}N_4O_2$ Calculated: C% 63.21; H% 3.76; N% 21.06; Found: C% 63.01; H% 4.02; N% 21.16.

EXAMPLE 9

Preparation of (2'-amino-4'-hydroxy-3',5'-dimethyl phenyl)-2-azo pyridine N-oxide of the formula

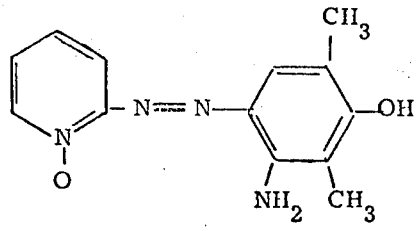

There is slowly added, with agitation, a solution of 0.1 mol of the diazonium salt prepared in accordance with the method referred to in Example 1, to a solution, maintained at 5°C, of 13.7 g of 3-amino-2,6-dimethyl phenol in 120 cc of a 10% sodium hydroxide solution. The reaction mixture is left to stand for one hour at ambient temperature at which time it is neutralized by the addition thereto of acetic acid. The thus formed dye is salted out by the addition of sodium chloride up to saturation. After filtering off the thus salted out dye and recrystallizing the same in methanol, the thus obtained product, which is deep red in color, melts at

EXAMPLE 10

Preparation of (3'-methyl-1'-phenyl-5'pyrazolone)-4':2-azo-1-methoxy pyridinium perchlorate of the formula

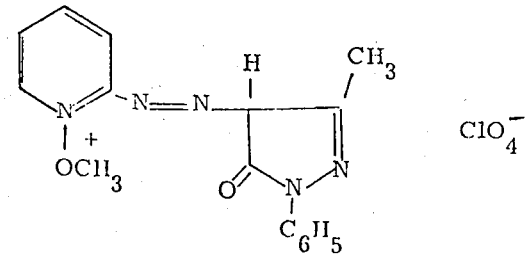

There are heated at 60°C for a period of twenty hours a solution of 2.95 g of 3-methyl-1'-phenyl-5'-pyrazolone-4':2-azo pyridine N-oxide and 6 cc of dimethyl sulfate in 75 cc of dimethylformamide. To the reaction mixture there is added 200 cc of sulfuric ether and the oil which separates therefrom is decanted and dissolved in 20 cc of water. The product is precipitated by the addition of a solution of 5 g of sodium perchlorate in 20 cc of water. The precipitate is filtered and dried on phosphoric anhydride to produce a yellow product melting with decomposition at 248°C.

EXAMPLE 11

Preparation of (2'-nitro-4'-dimethylamino phenyl)-2-azo-1-methoxypyridinium methylsulfate of the formula

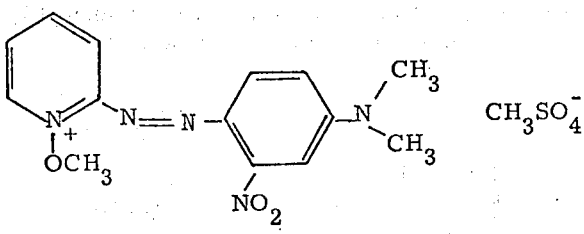

There is heated for a period of two hours at 80°C a suspension of 2.9 g of the product of Example 7 in a solution of 2.5 cc of methylsulfate and 60 cc of toluene. After cooling the same, the precipitate which forms is filtered and abundantly washed with toluene. After recrystallization in ethanol the above product exhibits a melting point of 180°C.

Analysis: $C_{15}H_{19}N_5O_7S$ Calculated: C% 43.60; H% 4.60; N% 16.92; Found: C% 43.33; H% 4.73; N% 16.95.

EXAMPLE 12

Preparation of (2',4'-diamino-5'-methyl phenyl)-2-azo-1-methoxy pyridinium perchlorate of the formula

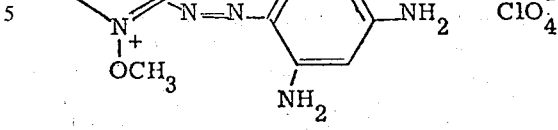

There are added 4 cc of dimethyl sulfate to a suspension of 3.5 g of (2',4'4'-diamino-5'-methyl phenyl) 2-azo pyridine N-oxide in 30 cc of O-dichlorobenzene. The resulting mixture is heated to 60°C while following the course of the reaction by thin layer chromotography. On completion of the reaction, the precipitate formed in the reaction mixture is filtered and washed, in petroleum ether, the crystals thus obtained having a brown color. These crystals are dissolved in water and re-precipitated by the addition thereto of a saturated solution of sodium perchlorate. The thus obtained perchlorate is washed with water and extracted with cold methanol. Concentration of the extract provides brownish red crystals having a melting point with decomposition of 175°C.

EXAMPLE 13

Preparation of (2',5'-dimethyl-4'-hydroxy phenyl)-2-azo pyridine N-oxide of the formula:

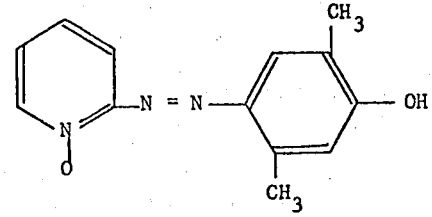

There is slowly added, with agitation and while maintaining the temperature at 5°C, a solution of 0.1 mol of the diazonium salt prepared in accordance with the method referred to in Example 1, to a solution of 12.2 g of 2,5-dimethyl phenol in 180 cc of a 10% sodium hydroxide solution. The reaction mixture is left to stand for one hour at ambient temperature at which time the brown precipitate which has formed is filtered therefrom.

The filtrate is acidified to a pH of 4.4 by the addition thereto of acetic acid. A precipitate forms which is then filtered, washed with cold water and dried on phosphoric anhydride. After recrystallization in a 70/30 ethanol-water mixture, red crystals melting at 250°C are recovered.

Analysis: $C_{13}H_{13}N_3O_2$ Calculated: N% 17.25; Found: N% 17.40; N% 17.33.

EXAMPLE 14

Preparation of (2'-dimethylamino-4'-hydroxy phenyl)-2-azo pyridine N-oxide and (4'-dimethylamino-2'-hydroxy phenyl)-2-azo pyridine N-oxide of the following formulae, respectively:

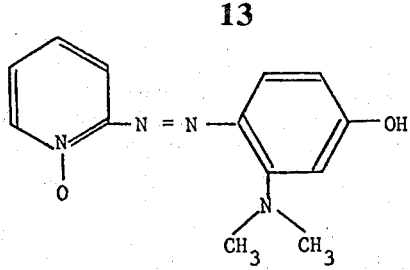

(A)

and

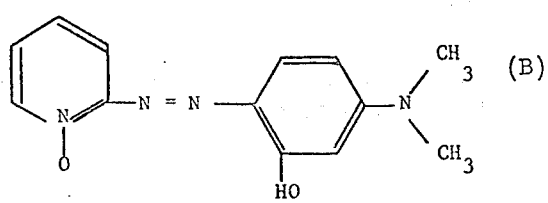

(B)

There is slowly added, while maintaining the temperature at 5°C, a solution of 0.1 mol of the diazonium salt prepared in accordance with the method referred to in Example 1, to a solution of 13.7 g of 3-hydroxy-N,N-dimethylaniline in 12 cc of acetic acid. The reaction mixture is left to stand for one hour at ambient temperature at which time it is neutralized by the addition thereto of sodium bicarbonate. The mineral salts thus formed are filtered and the resulting filtrate is extracted with chloroform. By concentrating the extracts there is obtained a brownish violet residue which is purified by recrystallization in methanol. The product, which is recrystallized with ½ mol of methanol, melts at 201°C and is in the form of orange crystals.

Analysis: Calculated: C% 59.2; H% 5.85; N% 20.5; Found: C% 58.94; H% 5.45; N% 20.83; C% 57.95; H% 5.81; N% 20.39.

Concentration of the methanol solutions and recrystallization in methanol provides, besides, a red product which is (4'-dimethylamino-2'-hydroxy phenyl)-2-azo pyridine N-oxide which melts at 170°C.

Analysis: Calculated: C% 59.20; H% 5.85; N% 20.5; Found: C% 59.93; H% 5.74 N% 20.53; C% 59.37; H% 5.50 N% 20.85.

EXAMPLE 15

Preparation of (4'-dimethylamino phenyl)-2-azo-5-nitro pyridine N-oxide of the formula

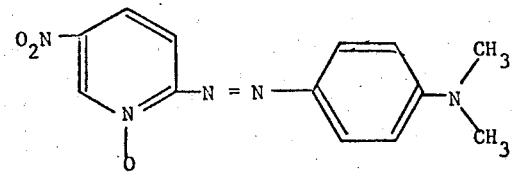

3.1 g of 2-amino-5-nitro pyridine N-oxide are dissolved in 50 ml of 85% orthophosphoric acid and the resulting solution is slightly heated. The solution is then cooled to −10°C and there are added thereto 1.52 g of sodium nitrite over a 30 minute period. The reaction mixture is then left to stand, with agitation, at −10°C for ½ hour. There is then slowly added, while maintaining the temperature at −10°C, the solution of the diazonium salt thus obtained to a solution of 2.42 g (0.02 mol) of N,N-dimethylaniline in 70 ml of ethyl alcohol. The mixture is left to react for 3 hours at −10°C at which time there are added 63 g of sodium acetate and 100 ml of water. The resulting mixture is agitated for a period of ten minutes, during which period a precipitate forms and at the end of which period the said precipitate is filtered. The precipitate is purified by recrystallization in methanol and it exhibits a melting point of 210°C.

EXAMPLE 16

Preparation of (4'-dimethylamino phenyl)-2-azo-6-methyl pyridine N-oxide of the formula

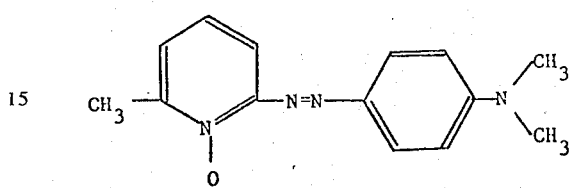

2-amino-6-methyl pyridine N-oxide is prepared in accordance with the method described by Adams in JACS, 76 (1954), 2785. To a solution of 0.033 mol of this compound in 30 ml of 5NHCl there are added at a temperature between 0°–5°C, 5 ml of 7.5N sodium nitrite. The resulting reaction mixture is left to stand for 30 minutes at which time the excess nitrite is eliminated by the addition thereto of sulfamic acid. There is then slowly added, while maintaining the temperature at 5°C, the solution of the diazonium salt thus obtained at a solution of 4 g of N,N-dimethylaniline in 6 ml of acetic acid. The reaction mixture is left to stand at ambient temperature for a period of about one hour at which time the reaction mixture is neutralized by the addition thereto of sodium bicarbonate. The precipitate which forms is then filtered, washed with water and then purified by recrystallization in a 15/85 mixture of ethanol and water. The above resulting product exhibits a melting point of 170°C.

EXAMPLE 17

Preparation of (4'-amino naphthalene)-1:2-azo-6-methyl pyridine N-oxide of the formula

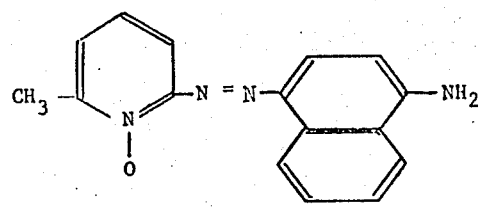

There is slowly added, while maintaining the temperature at 5°C, a solution of 0.033 mol of the diazonium salt prepared in accordance with the method set forth in Example 16, to a solution of 4.7 g of α-naphthylamine in 20 ml of acetic acid. The reaction mixture is left to stand for one hour at ambient temperature at which time there are then added 40 g of sodium acetate in 50 ml of water. The precipitate which forms is filtered, washed with water and purified by heating in acetone and then washing with ether. The product melts at 195°C.

EXAMPLE 18

Preparation of [4'-bis-(β-hydroxyethyl) amino phenyl]-2-azo-6-methyl pyridine N-oxide of the formula

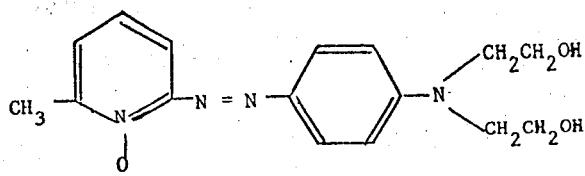

There is slowly added, while maintaining the temperature at 5°C, a solution of 0.033 mol of the diazonium salt prepared in accordance with the method set forth in Example 16, to a solution of 6 g of N,N-bis-(β-hydroxyethyl) aniline in 10 ml of acetic acid. The reaction mixture is left to stand for one hour at ambient temperature at which time it is neutralized by the addition thereto of sodium bicarbonate. The precipitate which forms is filtered, washed with water and dried on phosphoric anhydride. After recrystallization in 0.1N HCl, the resulting product exhibits a melting point of 204°C.

Analysis: $C_{16}H_{20}O_3N_4$
Calculated: C% 60.77; H% 6.33; N% 17.71;
Found: C% 60.53; H% 6.34; N% 17.51.

EXAMPLE 19

Preparation of (4'-diethylamino phenyl)-2-azo-6-methyl pyridine N-oxide of the formula

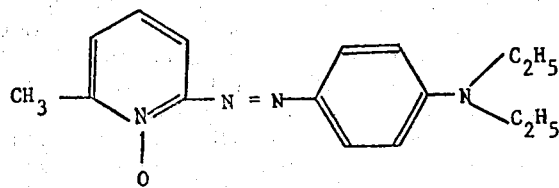

There is slowly added, while maintaining the temperature at 5°C, a solution of 0.033 mole of the diazonium salt prepared in accordance with Example 16, to a solution of 4.9 g of N,N-diethylaniline in 6 ml of acetic acid. The reaction mixture is left to stand at ambient temperature for one hour at which time it is neutralized by the addition thereto of sodium bicarbonate. The precipitate which forms is filtered and dried under a vacuum. After recrystallizing the same in isopropanol, the resulting product exhibits a melting point of 160°C.

Analysis: Calculated: C% 67.60; H% 7.04; N% 19.70; Found: C% 67.82; H% 7.23; N% 19.63.

EXAMPLE 20

Preparation of (2',5'-dimethyl-4'-hydroxy phenyl)-2-azo-6-methyl pyridine N-oxide of the formula

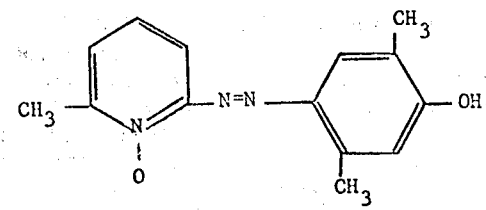

There is slowly added, while maintaining the temperature at 5°C, a solution of 0.03 mol of the diazonium salt prepared in accordance with Example 16, to a solution of 4.05 g of 2,5-dimethyl phenol in 90 ml of a 10% solution of sodium hydroxide. The reaction mixture is left to stand for one hour at ambient temperature. The precipitate which forms is then filtered and the resulting filtrate is acidified by the addition thereto of acetic acid. The precipitate which forms is then filtered, washed with water and dried. The resulting dye is dissolved in methanol from which it is reprecipitated by the addition thereto of water. The resulting product recrystallizes with ½ mol of methanol and melts at 222°C.

Analysis: $C_{14}H_{15}O_2N_3 \cdot$ ½ $CH_3OH$ Calculated: C% 63.70; H% 5.85; N% 15.40; Found: C% 63.51; H% 5.72; N% 15.56.

EXAMPLE 21

Preparation of [4'-bis-(β-hydroxyethyl)amino phenyl]-2-azo-4-methyl pyridine N-oxide of the formula

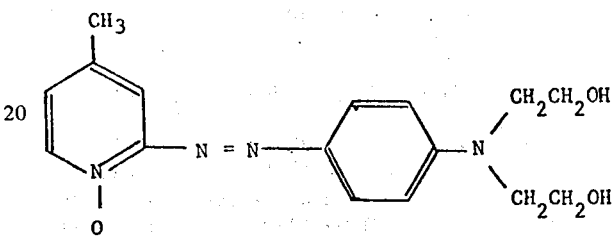

Step 1 — Preparation of 2-acetamido-4-methyl pyridine 5.4 g (0.051 mol) of 2-amino-4-methyl pyridine are dissolved in 9.5 ml of acetic anhydride. The resulting mixture is heated to reflux for one hour, poured into water and neutralized by the addition thereto of sodium bicarbonate. The product is precipitated by dissolving the mixture in benzene and reprecipitation by petroleum ether. The product melts at 99°C. Its molecular weight found by potentiometric dosage by N/10 $HClO_4$=150 (Theory, M. W. = 150).

Step 2 — Preparation of 2-acetamido-4-methyl pyridine N-oxide 4.3 g of 2-acetamido-4-methyl pyridine (prepared above) are dissolved in 8.6 ml of 20% peracetic acid. The resulting mixture is heated at 60°–70°C for 7 hours and then evaporated to dryness. The oily residue is recrystallized in benzene and the resulting product exhibits a melting point of 135°C.

Analysis: Calculated: C% 57.8; H% 6.02; N% 16.86; Found: C% 57.95; H% 6.37; N% 17.10.

Step 3

4.15 g (0.025 mol) of 2-acetamido-4-methyl pyridine N-oxide (prepared in Step 2) are heated to reflux for 1 hour with 25 ml of 5NHCl. The solution is then cooled to 5°C and there are slowly added 5 ml of 7.5N sodium nitrite. The reaction mixture is left to react for 30 minutes at which time the excess nitrous acid is eliminated by the addition thereto of sulfonic acid.

There is slowly added, while maintaining the temperature at 5°C, the solution of the diazonium salt thus obtained to a solution of 4.52 g of N,N-bis-(β-hydroxyethyl) aniline in 7.5 ml of acetic acid. The reaction mixture is left to stand for one hour at ambient temperature at which time it is neutralized by the addition thereto of sodium bicarbonate. The precipitate which forms is filtered, washed with water and dried. The product is purified by dissolving it in methanol and reprecipitation by water. The product melts at 218°C.

Analysis: Calculated: C% 60.77; H% 6.33; N% 17.71; Found: C% 60.88; H% 6.35; N% 17.5.

EXAMPLE 22

Preparation of (4'-diethylamino phenyl)-2-azo-4-methyl pyridine N-oxide of the formula

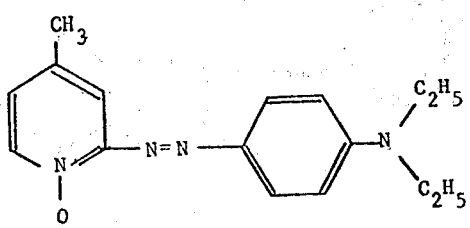

There is slowly added, while maintaining the temperature at 5°C, a solution of 0.025 mol of the diazonium salt prepared in accordance with Example 21, to a solution of 3.72 g of N,N-diethylaniline in 5 ml of acetic acid. The reaction mixture is left to stand for one hour at ambient temperature at which time it is neutralized by the addition thereto of sodium bicarbonate. An oil phase appears which is then extracted with chloroform. By concentrating the extract there is obtained a brown residue, which after recrystallization in a 30/70 mixture of methanol and water, followed by washing with ether and acetone, exhibits a melting point of 175°C. Its molecular weight found by potentiometric dosage in N/10 $HClO_4$ = 286.5 (Theory, M.W. = 284).

EXAMPLE 23

Preparation of (4'-amino naphthalene)-1':2-azo-4-methyl pyridine N-oxide of the formula

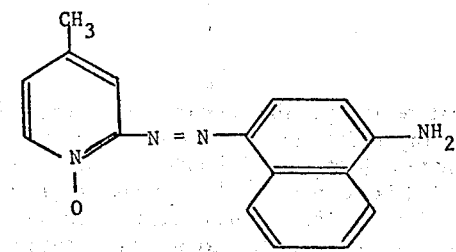

There is slowly added, while maintaining the temperature at 5°C, a solution of 0.025 mol of the diazonium salt prepared in Example 21, to a solution of 3.58 g of α-naphthylamine in 15 ml of acetic acid. The reaction mixture is left to stand for one hour at ambient temperature at which time there are added 40 g of sodium acetate dissolved in 50 ml of water. A precipitate forms which is then filtered, washed with water, then with a minimum of acetone and finally with ether. The thus washed product is dried on phosphoric anhydride and exhibits a melting point of 197°C. Its molecular weight found by potentiometric dosage in N/10 $HClO_4$ = 279 (Theory, M.W. = 278).

EXAMPLE 24

Preparation of (2',4'-diamino-5'-methyl phenyl)-2-azo-4-methyl pyridine N-oxide of the formula

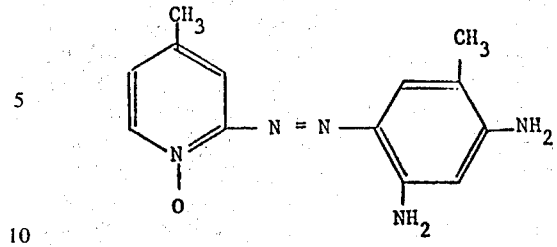

There is slowly added, while maintaining the temperature at 5°C, a solution of 0.025 mol of the diazonium salt prepared according to Example 21, to a solution of 3.04 g of 1,3-diamino-4-methyl benzene in 6.5 ml of acetic acid. The reaction mixture is left to stand for one hour at ambient temperature, at which time, the precipitate which has formed is filtered. The product is purified by washing with methylethyl ketone and recrystallization in pyridine. It recrystallizes with 0.4 mol of pyridine and its melting point is 193°C.

Analysis: $C_{13}H_{15}O \ N_5 \cdot 0.4C_5H_5N$ Calculated: C% 62.10; H% 5.89; N% 26.10; Found: C% 61.96; H% 5.71; N% 25.80; C% 61.81; H% 5.60; N% 25.88.

EXAMPLE 25

Preparation of (4'-dimethylamino phenyl)-2-azo-4-methyl pyridine N-oxide of the formula

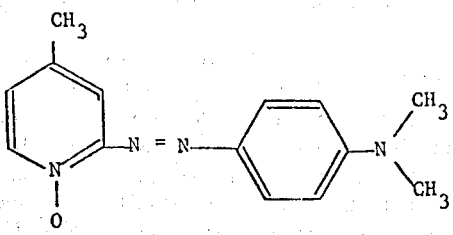

There is slowly added, while maintaining the temperature at 5°C, a solution of 0.0287 mol of the diazonium salt prepared in accordance with Example 21, to a solution of 0.0287 mol of N,N-dimethylaniline in 5 ml of acetic acid. The reaction mixture is left to stand for one hour at ambient temperature at which time it is neutralized by the addition thereto of sodium bicarbonate. The precipitate which forms is filtered and purified by recrystallization in a 50/50 mixture of methanol and water. The product melts at 198°C.

Analysis: $C_{14}H_{16}O \ N_4$ Calculated: N% 21.9; Found: N% 22.01; N% 22.05.

EXAMPLE 26

Preparation of (2',5'-dimethyl-4'-hydroxy phenyl)-2-azo-4-methyl pyridine N-oxide of the formula

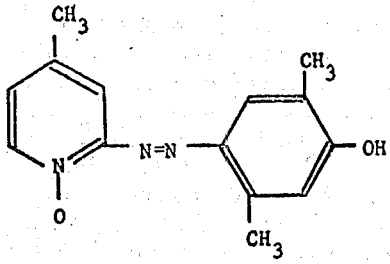

There is slowly added, while maintaining the temperature at 5°C, a solution of 0.025 mol of the diazonium salt prepared in accordance with Example 21, to a solution of 3.04 g of 2,5-dimethyl phenol in 80 ml of 10% sodium hydroxide. The reaction mixture is left to stand for one hour at ambient temperature and the precipitate which forms is filtered therefrom. The resulting filtrate is acidified with acetic acid and the precipitate which forms is then filtered, washed with water and dried. The product is purified by recrystallization in a 50/50 mixture of methanol and water. It crystallizes with a half mol of methanol and exhibits a melting point of 200°C.

Analysis: $C_{14}H_{15}O_3N_3 \cdot 0.5CH_3OH$ Calculated: C% 63.70; H% 5.85; N% 15.40; Found: C% 63.36; H% 6.00; N% 15.30.

EXAMPLE 27

Preparation of (4'-dimethylamino phenyl)-2-azo-5-chloro pyridine N-oxide of the formula

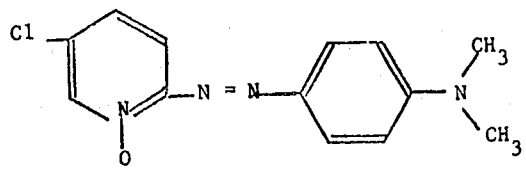

Step 1 — Preparation of 2-acetamido-5-chloro pyridine 12.85 g (0.1 mol) of 2-amino-5-chloro pyridine in 20 ml of benzene are heated with 10 ml of acetic anhydride using a water-bath for one hour. The reaction mixture is then cooled and filtered to recover the precipitate which forms, which precipitate is dried and exhibits a melting point of 171°–172°C. Its molecular weight found by potentiometric dosage in N/10 $HClO_4$ = 173.5.

Step 2 — Preparation of 2-acetamido-5-chloro pyridine N-oxide 6 g of 2-acetamido-5-chloro pyridine (prepared in step 1) are heated with 8 ml of 30% peracetic acid for 7 hours at 60°–70°C. The reaction mixture is then evaporated to dryness and the resulting residue is recrystallized in methanol. Its melting point is 150°–151°C.

Step 3 — Preparation of 2-amido-5-chloro pyridine N-oxide 2 g of 2-acetamido-5-chloro pyridine N-oxide (prepared in step 2) and 9 ml of 5N HCl are heated to reflux for one hour. The reaction mixture is then cooled and neutralized by the addition thereto of sodium bicarbonate.

Step 4

2.8 g (0.02 mol) of 2-amino-5-chloro pyridine N-oxide (prepared in step 3) are dissolved in 14 ml of 5N HCl and 10 ml of water. There are slowly added, while maintaining the temperature at 5°C, 3 ml of 7.5 N sodium nitrite. The reaction mixture is left to react for 30 minutes at which time the excess nitrite is eliminated by the addition of sulfamic acid.

There is slowly added the solution thus obtained to a solution of 0.02 mol of N,N-dimethylaniline in 5 ml of acetic acid. The reaction mixture is left to stand at ambient temperature for one hour at which time the precipitate which forms is filtered, and washed with water and sulfuric ether. The product thus obtained melts at 172°C.

EXAMPLE 28

Preparation of (6'-hydroxy benzomorpholine)-7':2-azo pyridine N-oxide of the formula

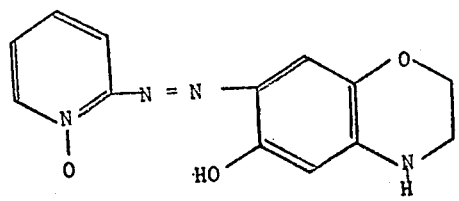

There is added, with agitation and while maintaining the temperature at 5°C, a solution of 0.1 mol of the diazonium salt prepared in accordance with Example 1, to a solution of 15.1 g of 6-hydroxy benzomorpholine in 15 cc of acetic acid. The reaction mixture is left to stand for one hour at ambient temperature at which time there are added 100 cc of a 40% aqueous solution of sodium acetate. The precipitate which forms is filtered, washed with methanol and dried. The resulting product, after recrystallization in methanol, melts at 210°C.

EXAMPLE 29

Preparation of (6'-hydroxy benzomorpholine)-7':2-azo-1-methoxy pyridinium methyl sulfate of the formula

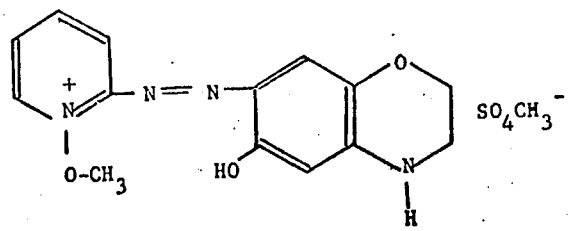

A mixture of 1 g of the compound of Example 28, 2 cc of methyl sulfate and 25 cc of anhydrous dimethylformamide is heated for 8 hours at 50°C. There are then added 2 cc of methyl sulfate and heating is continued for 12 hours. There is then added thereto a mixture of ethanol and sulfuric ether to precipitate the product which is then filtered, washed with sulfuric ether and dried. The product melts at 222°C.

EXAMPLE 30

Preparation of (2',4'-diamino-5'-methyl phenyl)-2-azo pyridine N-oxide of the formula

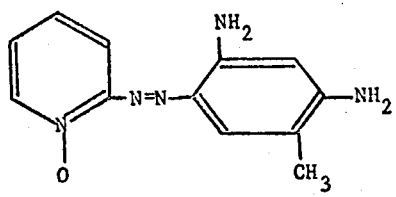

There is slowly added, with agitation and while maintaining the temperature at +10°C, a solution of 0.1 mol of the diazonium salt prepared in accordance with Example 1, to a solution of 13.1 g of m-toluenediamine in 25 cc of acetic acid. The reaction mixture is left to stand for one hour at ambient temperature at which time the precipitate which forms is filtered, washed with acetone and dried on phosphoric anhydride. After purifying the same by treatment with boiling pyridine, the product exhibits a melting point of 245°–250°C.

EXAMPLE 31

A hair setting lotion is prepared as follows:

| | |
|---|---|
| Copolymer of 70% vinyl pyrrolidone - 30% vinyl acetate (MW = 35,000–45,000) | 2 g |
| Ethyl alcohol | 50 cc |
| Triethanolamine, q.s.p. | pH 7 |
| (3'-methyl-1'-phenyl-5-pyrazolone)-4':2-azo pyridine N-oxide | 0.0075 g |
| Water, q.s.p. | 100 cc |

This hair setting lotion when applied to bleached hair imparts thereto a particularly esthetic light golden blond coloration.

EXAMPLE 32

A hair setting lotion is prepared as follows:

| | |
|---|---|
| Copolymer of vinyl pyrrolidone-vinyl acetate (Example 31) | 2.5 g |
| Ethyl alcohol | 50 cc |
| Triethanolamine, q.s.p. | pH 8.5 |
| (2'-hydroxynaphthalene)-1':2-azo-1-methoxy pyridinium methyl sulfate | 0.040 g |
| Water, q.s.p. | 100 cc |

This hair setting lotion when applied to natural blond hair imparts thereto a particularly luminous and esthetic pearly blond coloration.

EXAMPLE 33

The following composition is prepared:

| | |
|---|---|
| Copolymer of 90% vinyl acetate - 10% crotonic acid (MW = 45,000–50,000) | 2 g |
| Ethyl alcohol | 50 cc |
| Benzylidene camphor | 0.2 g |
| Triethanolamine, q.s.p. | pH 8 |
| (4'-dimethylamino phenyl)-2-azo-pyridine N-oxide | 0.020 g |
| (3'-methyl-1'-phenyl-5'-pyrazolone)-4':2-azo pyridine N-oxide | 0.010 g |
| (2'-hydroxy naphthalene)-1':2-azo-1-methoxy pyridinium methyl sulfate | 0.030 g |
| Water, q.s.p. | 100 cc |

This hair setting lotion when applied to light mahogany colored hair imparts thereto particularly luminous and esthetic coppery mahogany glints.

EXAMPLE 34

The following composition is prepared:

| | |
|---|---|
| Copolymer of vinyl acetate-crotonic acid (Example 33) | 2 g |
| Ethyl alcohol | 50 cc |
| Benzylidene camphor | 0.2 g |
| (4'-dimethylamino phenyl)-2-azo pyridine N-oxide | 0.025 g |
| Triethanolamine, q.s.p. | pH 7.5 |
| Water, q.s.p. | 100 cc |

This hair setting lotion when applied to chestnut colored hair imparts thereto a very luminous coppery chestnut coloration.

EXAMPLE 35

The following composition is prepared:

| | |
|---|---|
| Copolymer of vinylpyrrolidone-vinyl acetate (ex. 31) | 0.5 g |
| Hydroxyethylcellulose (sold under the trade name "Natrosol 250 L") | 0.50 g |
| Dye of Example 11 | 0.015 g |
| Citric acid, q.s.p. | pH 5 |
| Water, q.s.p. | 100 cc |

This hair rinse lotion when applied to natural chestnut colored hair imparts thereto particularly esthetic and luminous ashen glints.

EXAMPLE 36

The following composition is prepared:

| | |
|---|---|
| Hydroxyethylcellulose (sold under the trade name "Natrosol 250 L") | 0.7 g |
| Dye of Example 29 | 0.090 g |
| Dye of Example 10 | 0.010 g |
| Citric acid, q.s.p. | pH 6 |
| Water, q.s.p. | 100 cc |

This hair rinse lotion when applied to blond hair imparts thereto a particularly esthetic iridescent blond coloration.

EXAMPLE 37

The following composition is prepared:

| | |
|---|---|
| Polyvinylpyrrolidone (MW = 40,000) | 0.5 g |
| Dye of Example 12 | 0.030 g |
| (4'-diethylamino phenyl)-2-azo-1-methoxy pyridinium methyl sulfate | 0.020 g |
| Dye of Example 10 | 0.005 g |
| Citric acid, q.s.p. | pH 3 |
| Water, q.s.p. | 100 cc |

This composition when applied to deep chestnut colored hair for a period of 20 minutes, and after rinsing, imparts thereto a particularly luminous and esthetic violet coloration.

EXAMPLE 38

The following composition is prepared:

| | |
|---|---|
| Hydroxyethylcellulose (sold under the trade name "Natrosol 250 L") | 0.8 g |
| Ethyl cellosolve | 10 cc |
| Dye of Example 2 | 0.1 g |
| Citric acid, q.s.p. | pH 4 |
| Water, q.s.p. | 100 cc |

This hair dye composition when applied for a period of 10 minutes to strongly and freshly bleached hair imparts thereto, after rinsing a particularly esthetic light golden blond coloration.

EXAMPLE 39

The following composition is prepared:

| | |
|---|---|
| Copolymer of vinyl acetate - crotonic acid (Example 33) | 2.0 g |
| Ethyl alcohol - q.s.p. 50° | |
| (3'-methyl-1'-phenyl-5'-pyrazolone)-4':2-azo pyridine N-oxide | 0.010 g |
| (2'-hydroxy naphthalene)-1':2-azo-1-methoxy pyridinium methyl sulfate | 0.020 g |
| Triethanolamine, q.s.p. | pH 7 |
| Water, q.s.p. | 100 cc |

This hair setting lotion when applied to golden blond hair imparts thereto particularly esthetic pearly golden glints.

EXAMPLE 40

The following composition is prepared:

| | |
|---|---|
| Hydroxyethylcellulose (sold under the trade name "Natrosol 250 L") | 2 g |
| Dye of Example 29 | 0.080 g |
| Dye of Example 10 | 0.010 g |
| Citric acid, q.s.p. | pH 3 |
| Water, q.s.p. | 100 cc |

This dye composition when applied to very light blond hair for a period of 10 minutes imparts to said hair, after rinsing, a light pearly blond coloration.

EXAMPLE 41

The following composition is prepared:

| | |
|---|---|
| Hydroxyethylcellulose (sold under the trade name "Natrosol 250 L") | 0.5 g |
| Polyvinylpyrrolidone (MW = 40,000) | 0.3 g |
| Dye of Example 30 | 0.030 g |
| Triethanolamine, q.s.p. | pH 7 |
| Water, q.s.p. | 100 cc |

This hair rinse lotion when applied to chestnut colored hair imparts thereto a very luminous mahogany chestnut coloration.

EXAMPLE 42

The following composition is prepared:

| | |
|---|---|
| Dye of Example 12 | 0.030 g |
| (4'-diethylamino phenyl)-2-azo-1 methoxy pyridinium methyl sulfate | 0.020 g |
| Dye of Example 10 | 0.005 g |
| Triethanolamine, q.s.p. | pH 8.5 |
| Water, q.s.p. | 100 cc |

This hair rinse lotion when applied to black hair imparts thereto particularly esthetic violet glints, the resistance of which to shampooing is excellent.

EXAMPLE 43

The following composition is prepared:

| | |
|---|---|
| Copolymer of vinylpyrrolidone-vinyl acetate (Example 31) | 2.0 g |
| Polyvinylpyrrolidone (MW = 40,000) | 0.5 g |
| (4'-dimethylamino phenyl)-2-azo-1-methoxy pyridinium methyl sulfate | 0.036 g |
| Ethyl alcohol | 50 cc |
| Triethanolamine, q.s.p. | pH 8 |
| Water, q.s.p. | 100 cc |

This hair setting lotion when applied to chestnut colored hair imparts thereto very esthetic ashen glints.

EXAMPLE 44

The following composition is prepared:

| | |
|---|---|
| Dye of Example 29 | 0.035 g |
| Water, q.s.p. | 100 cc |

This hair rinse lotion having a pH of 7 when applied to blond hair, imparts thereto very esthetic pearly glints.

EXAMPLE 45

The following composition is prepared:

| | |
|---|---|
| Dye of Example 5 | 0.1 g |
| Ethyl cellosolve | 10 cc |
| Triethanolamine, q.s.p. | pH 8.5 |
| Water, q.s.p. | 100 cc |

This composition when applied to light chestnut colored hair for 20 minutes, imparts thereto, after rinsing, a coppery light chestnut coloration.

EXAMPLE 46

The following composition is prepared:

| | |
|---|---|
| (4'-diethylamino phenyl)-2-azo pyridine N-oxide | 0.030 g |
| Citric acid, q.s.p. | pH 3 |
| Water, q.s.p. | 100 cc |

This hair rinse lotion when applied to deep blond hair imparts thereto a deep pearly rose blond coloration.

EXAMPLE 47

The following composition is prepared:

| | |
|---|---|
| Dye of Example 6 | 0.1 g |
| Ethyl cellosolve | 10 cc |
| Triethanolamine, q.s.p. | pH 9 |
| Water, q.s.p. | 100 cc |

This hair rinse lotion when applied to blond hair imparts thereto a particularly esthetic pearly blond coloration.

EXAMPLE 48

The following composition is prepared:

| | |
|---|---|
| Dye of Example 1 | 0.026 g |
| Triethanolamine, q.s.p. | pH 8.5 |
| Water, q.s.p. | 100 cc |

This hair rinse lotion when applied to natural blond hair imparts thereto a pearly blond coloration.

EXAMPLE 49

The following composition is prepared:

| | |
|---|---|
| (4'-diethylamino phenyl)-2-azo-1-methoxy pyridinium methyl sulfate | 0.050 g |
| Ethyl alcohol | 50 cc |
| $H_2O_2$ (200 volumes) | 5 cc |
| Orthophosphoric acid, q.s.p. | pH 3 |
| Water, q.s.p. | 100 cc |

This hair rinsing lotion when applied to natural light chestnut colored hair, lightens it and at the same time imparts thereto very luminous ashen glints.

EXAMPLE 50

The following composition is prepared:

| | |
|---|---|
| Dye of Example 29 | 0.030 g |
| (4'-diethylamino phenyl)-2-azo-1-methoxy pyridinium methyl sulfate | 0.020 g |
| Dye of Example 7 | 0.025 g |
| Ethyl alcohol | 50 cc |
| $H_2O_2$ (200 volumes) | 5 cc |
| Orthophosphoric acid, q.s.p. | pH 3 |
| Copolymer of vinyl acetate-crotonic acid (Example 33) | 2.0 g |

-continued

| | |
|---|---|
| Water q.s.p. | 100 cc |

This hair setting lotion when applied to natural blond hair imparts thereto a particularly esthetic pearly blond coloration.

EXAMPLE 51

The following composition is prepared:

| | |
|---|---|
| Copolymer of vinylpyrrolidone-vinyl acetate (Example 31) | 2.0 g |
| Dye of Example 29 | 0.035 g |
| Ethyl alcohol | 50 cc |
| H$_2$O$_2$ (200 volumes) | 5 cc |
| Orthophosphoric acid, q.s.p. | pH 3 |
| Water, q.s.p. | 100 cc |

This hair setting lotion when applied to light blond hair, not only lightens the hair but imparts thereto pearly golden glints.

EXAMPLE 52

The following composition is prepared:

| | |
|---|---|
| Dye of Example 29 | 0.035 g |
| (4'-dimethylamino phenyl)-2-azo-1-methoxy pyridinium methyl sulfate | 0.018 g |
| H$_2$O$_2$ (200 volumes) | 5 cc |
| Ethyl alcohol | 50 cc |
| Orthophosphoric acid, q.s.p. | pH 3 |
| Water, q.s.p. | 100 cc |

This hair rinse lotion when applied to natural light chestnut colored hair slightly lightens it and imparts thereto ashen glints.

EXAMPLE 53

The following composition is prepared:

| | |
|---|---|
| (4'-dimethylamino phenyl)-2-azo pyridine N-oxide | 1.0 g |
| Butyl cellosolve | 8 g |
| Propylene glycol | 8 g |
| Polyethoxyether of nonylphenol (sold under the trade name "REMCOPAL 334") | 22 g |
| Polyethoxyether of nonylphenol sold under the trade name "REMCOPAL 349") | 22 g |
| Ammonia, 22° Bé | 10 g |
| Water, q.s.p. | 100 g |

To 20 g of the above composition there are added 20 g of H$_2$O$_2$ (20 volumes) to produce a gel which is applied to chestnut colored hair for a period of about 30 minutes. After washing and drying the thus treated hair, there is imparted thereto a reddish violet light chestnut coloration.

EXAMPLE 54

The following composition is prepared:

| | |
|---|---|
| (4'-dimethylamino phenyl)-2-azo pyridine N-oxide | 1.0 g |
| Butyl cellosolve | 8 g |
| Propylene glycol | 8 g |
| Polyethoxyether of nonylphenol (sold under the trade name "REMCOPAL 334") | 22 g |
| Polyethoxyether of nonylphenol (sold under the trade name "REMCOPAL 349") | 22 g |
| Ammonia, 22° Bé | 10 g |
| Water, q.s.p. | 100 cc |

To 30 g of the above composition there are added 30 g of water to produce a gel which is applied to deep chestnut colored hair for a period of about 40 minutes. After washing and drying the thus treated hair there is imparted thereto light violet reddish glints.

EXAMPLE 55

The following composition is prepared:

| | |
|---|---|
| Dye of Example 1 | 1.0 g |
| Butyl cellosolve | 8 g |
| Propylene glycol | 8 g |
| Polyethoxyether of nonylphenol (sold under the trade name "REMCOPAL 334") | 22 g |
| Polyethoxyether of nonylphenol (sold under the trade name "REMCOPAL 349") | 22 g |
| Ammonia, 22° Bé | 10 g |
| Water, q.s.p. | 100 g |

To 20 g of the above composition there are added 20 g of H$_2$O$_2$ (20 volumes) to produce a gel which is applied to deep blond hair for a period of about 30 minutes. After washing and drying the hair is lightened and exhibits a pearly blond coloration.

EXAMPLE 56

The following composition is prepared:

| | |
|---|---|
| (4'-dimethylamino phenyl)-2-azo pyridine N-oxide | 0.008 g |
| N-[(4'-amino-2'-methoxy-3',5',-dimethyl)phenyl]-3,6-dimethyl benzoquinoneimine | 0.024 g |
| N-[(4'-amino-3',5',dimethyl phenyl]-3-acetylamino-6-methyl benzoquinoneimine | 0.032 g |
| Copolymer of vinyl acetate-crotonic acid (Example 33) | 2.5 g |
| Ethyl alcohol | 50 cc |
| Triethanolamine, q.s.p. | pH 7 |
| Water, q.s.p. | 100 cc |

This hair setting lotion when applied to blond hair imparts thereto a very esthetic iridescent blond coloration.

EXAMPLE 57

The following composition is prepared:

| | |
|---|---|
| (4'-diethylamino phenyl)-2-azo-1-methoxy pyridinium methyl sulfate | 0.016 g |
| N-[(4'-hydroxy)phenyl]-3'-amino-6'-methyl benzoquinoneimine | 0.008 g |
| Toluene blue hydrochloride | 0.008 g |
| Polyvinylpyrrolidone (MW = 40,000) | 2.0 g |
| Ethyl alcohol | 50 cc |
| Triethanolamine, q.s.p. | pH 7 |
| Water, q.s.p. | 100 cc |

This hair setting lotion when applied to blond hair imparts thereto a particularly esthetic ash blond coloration.

EXAMPLE 58

The following composition is prepared:

| | |
|---|---|
| (4'-dimethylamino phenyl)-2-azo-1-methoxy pyridinium methyl sulfate | 0.008 g |
| Dye of Example 30 | 0.012 g |
| 4-methyl-8-β-hydroxyethylamino-[2,3-b] morpholino phenoxazonium bromide | 0.020 g |
| Butyl hydroxyanisole | 0.1 g |
| Copolymer of vinyl acetate - crotonic acid (Example 33) | 2 g |
| Benzylidene camphor | 0.2 g |
| Triethanolamine, q.s.p. | pH 7.5 |
| Ethyl alcohol | 50 cc |
| Water, q.s.p. | 100 cc |

This hair setting lotion when applied to deep blond hair, imparts thereto a pretty deep ash blond coloration.

EXAMPLE 59

The following composition is prepared:

| | |
|---|---|
| Dye of Example 1 | 0.010 g |
| N-1-methylamino-4-γ-aminopropyl-amino anthraquinone | 0.020 g |
| Copolymer of vinylpyrrolidone-vinyl acetate (Example 31) | 2.0 g |
| Ethyl alcohol | 50 cc |
| Triethanolamine, q.s.p. | pH 8 |
| Water, q.s.p. | 100 cc |

This hair setting lotion when applied to white hair imparts thereto very uniform and very esthetic ash gray glints.

EXAMPLE 60

The following composition is prepared:

| | |
|---|---|
| Dye of Example 1 | 0.001 g |
| (4'-diethylamino phenyl)-2-azo-1-methoxy pyridinium methyl sulfate | 0.008 g |
| Toluene blue hydrochloride | 0.004 g |
| N-[(4'-hydroxy)phenyl]-3-amino-6-metyl benzoquinoneimine | 0.004 g |
| Ethyl alcohol | 50 cc |
| Copolymer of vinylpyrrolidone-vinyl acetate (Example 31) | 2.0 g |
| Triethanolamine, q.s.p. | pH 8 |
| Water, q.s.p. | 100 cc |

This hair setting lotion when applied to light blond hair imparts thereto a particularly esthetic light ash blond coloration.

EXAMPLE 61

The following composition is prepared:

| | |
|---|---|
| (4'-dimethylamino phenyl)-2-azo-1-methoxy pyridinium methyl sulfate | 0.020 g |
| Nitroparaphenylene diamine | 0.006 g |
| Copolymer of vinyl acetate-crotonic acid (Example 33) | 2.0 g |
| Ethyl alcohol | 50 cc |
| Triethanolamine, q.s.p. | pH 7 |
| Water, q.s.p. | 100 cc |

This hair setting lotion when applied to natural deep chestnut colored hair imparts thereto violet glints which are particularly chatoyant.

EXAMPLE 62

The following composition is prepared:

| | |
|---|---|
| Copolymer of vinylpyrrolidone-vinyl acetate (Example 31) | 1.8 g |
| Dye of Example 15 | 0.020 g |
| Ethyl alcohol, q.s.p. 50° | |
| Triethanolamine, q.s.p. | pH 7 |
| Water, q.s.p. | 100 cc |

This hair setting lotion when applied to blond hair imparts thereto a very luminous and particularly esthetic ash blond coloration.

EXAMPLE 63

The following composition is prepared:

| | |
|---|---|
| Copolymer of vinylpyrrolidone-vinyl acetate (Example 31) | 0.50 g |
| Hydroxyethyl cellulose (sold under the trade name "Natrosol 250 L") | 0.5 g |
| Dye of Example 3 | 0.020 g |
| Ethyl cellosolve | 10 cc |
| Monoethanolamine, q.s.p. | pH 9.5 |
| Water, q.s.p. | 100 cc |

This hair rinse lotion when applied to strongly bleached hair imparts thereto a particularly esthetic pearly golden coloration.

EXAMPLE 64

The following composition is prepared:

| | |
|---|---|
| Copolymer of vinylpyrrolidone-vinyl acetate (Example 31) | 0.50 g |
| Hydroxyethylcellulose (sold under the trade name "Natrosol 250 L") | 0.50 g |
| Dye of Example 13 | 0.010 g |
| Butyl cellosolve | 10 cc |
| Monoethanolamine, q.s.p. | pH 9 |
| Water, q.s.p. | 100 cc |

This hair rinse lotion when applied to strongly bleached hair imparts thereto a slightly pearly very light blond coloration.

EXAMPLE 65

The following composition is prepared:

| | |
|---|---|
| Copolymer of vinyl acetate-crotonic acid (Example 33) | 2.0 g |
| Ethyl alcohol, q.s.p. 50° | |
| Triethanolamine, q.s.p. | pH 9 |
| Dye of Example 19 | 0.050 g |
| (4'-amino naphthalene)-1':2-azo pyridine N-oxide | 0.040 g |
| Dye of Example 15 | 0.080 g |
| Water, q.s.p. | 100 cc |

This hair setting lotion when applied to chestnut colored hair imparts thereto a particularly esthetic violet chestnut coloration.

EXAMPLE 66

The following composition is prepared:

| | |
|---|---|
| Hydroxyethylcellulose (sold under the trade name "Natrosol 250 L") | 0.8 g |
| Ethyl cellosolve | 10 cc |
| Dye of Example 16 | 0.020 g |
| Dye of Example 25 | 0.005 g |
| Monoethanolamine, q.s.p. | pH 8.5 |
| Water, q.s.p. | 100 cc |

This hair rinse solution when applied to coppery light chestnut colored hair imparts thereto a particularly esthetic coppery light mahogany chestnut coloration.

EXAMPLE 67

The following composition is prepared:

| | |
|---|---|
| Copolymer of vinyl acetate-crotonic acid (Example 33) | 2.0 g |
| Ethyl alcohol | 50 cc |
| Benzylidene camphor | 0.2 g |
| Triethanolamine, q.s.p. | pH 7 |
| Dye of Example 8 | 0.010 g |
| Dye of Example 22 | 0.005 g |
| Water, q.s.p. | 100 cc |

This hair setting lotion when applied to blond hair, imparts thereto very esthetic pearly glints.

EXAMPLE 68

The following composition is prepared:

| | |
|---|---|
| Copolymer of vinylpyrrolidone-vinyl acetate (Example 31) | 2.0 g |
| Dye of Example 20 | 0.016 g |
| Dye of Example 21 | 0.016 g |
| Ethyl alcohol, q.s.p. 50° | |
| Triethanolamine, q.s.p. | pH 7 |
| Water, q.s.p. | 100 cc |

This hair setting lotion when applied to light blond hair imparts thereto particularly esthetic pearly golden glints.

EXAMPLE 69

The following composition is prepared:

| | |
|---|---|
| Copolymer of vinylpyrrolidone-vinyl acetate (Example 31) | 2.0 g |
| Dye of Example 18 | 0.060 g |
| Dye of Example 17 | 0.100 g |
| Ethyl alcohol, q.s.p. 50° | |
| Triethanolamine, q.s.p. | pH 9 |
| Water, q.s.p. | 100 cc |

This hair setting lotion when applied to chestnut colored hair imparts thereto very luminous and very esthetic pearly glints.

EXAMPLE 70

The following composition is prepared:

| | |
|---|---|
| Copolymer of vinyl acetate-crotonic acid (Example 33) | 2.0 g |
| Dye B of Example 14 | 0.025 g |
| Ethyl alcohol | 50 cc |
| Triethanolamine, q.s.p. | pH 9.5 |
| Water, q.s.p. | 100 cc |

This hair setting lotion when applied to blond hair imparts thereto very esthetic pearly glints.

EXAMPLE 71

The following composition is prepared:

| | |
|---|---|
| Copolymer of vinyl acetate-crotonic acid (Example 33) | 2.5 g |
| Ethyl alcohol | 50 cc |
| $H_2O_2$ (200 volumes) | 5 cc |
| Orthophosphoric acid, q.s.p. | pH 3 |
| Dye of Example 4 | 0.040 g |
| Dye A of Example 14 | 0.040 g |
| Water, q.s.p. | 100 cc |

This hair setting lotion when applied to deep chestnut colored hair, lightens the hair and imparts thereto a particularly luminous coppery mahogany chestnut coloration.

EXAMPLE 72

The following composition is prepared:

| | |
|---|---|
| Copolymer of vinyl pyrrolidone-vinyl acetate (Example 31) | 2.0 g |
| $H_2O_2$ (200 volumes) | 5 cc |
| Orthophosphoric acid, q.s.p. | pH 3 |
| Dye of Example 27 | 0.040 g |
| Water, q.s.p. | 100 cc |

This hair setting lotion when applied to natural chestnut colored hair lightens the same and imparts thereto particularly luminous pearly glints.

EXAMPLE 73

The following composition is prepared:

| | |
|---|---|
| Copolymer of vinyl acetate-crotonic acid (Example 33) | 2.0 g |
| Ethyl alcohol | 50 cc |
| Triethanolamine, q.s.p. | pH 9.5 |
| Dye of Example 9 | 0.030 g |
| Dye of Example 23 | 0.020 g |
| Water, q.s.p. | 100 cc |

This hair setting lotion when applied to blond hair imparts thereto a particularly luminous pearly blond coloration.

EXAMPLE 74

The following composition is prepared:

| | |
|---|---|
| Copolymer of vinylpyrrolidone - vinyl acetate (Example 31) | 2.5 g |
| Ethyl alcohol | 50 cc |
| Triethanolamine, q.s.p. | pH 9.5 |
| Dye of Example 26 | 0.030 g |
| Dye of Example 18 | 0.030 g |
| Water, q.s.p. | 100 cc |

This hair setting lotion when applied to light chestnut colored hair imparts thereto a very luminous coppery mahogany chestnut coloration.

EXAMPLE 75

The following composition is prepared:

| | |
|---|---|
| Copolymer of vinylpyrrolidone-vinyl acetate (Example 31) | 2.0 g |
| Ethyl alcohol | 90 cc |
| Benzylidene camphor | 0.2 g |
| Triethanolamine, q.s.p. | pH 9 |
| Dye of Example 28 | 0.010 g |
| Water, q.s.p. | 100 cc |

This hair setting lotion when applied to strongly bleached hair imparts thereto pretty pearly light blond coloration.

EXAMPLE 76

The following composition is prepared:

| | |
|---|---|
| Copolymer of vinyl acetate-crotonic acid (Example 33) | 2.0 g |
| Ethyl alcohol | 50 cc |
| Triethanolamine, q.s.p. | pH 7 |
| Dye of Example 17 | 0.080 g |
| N-[(4'-amino-2'-methoxy-3',5'-dimethyl) phenyl]-2,5-dimethyl benzoquinoneimine | 0.040 g |
| Water, q.s.p. | 100 cc |

This hair setting lotion when applied to natural chestnut colored hair imparts thereto a particularly esthetic violet mahogany chestnut coloration.

What is claimed is:

1. A dye composition for human hair comprising a solution in a solvent selected from the group consisting of water and a hydroalcoholic solution of about 0.001–1 percent by weight of at least one dye selected from the group consisting of
    1. a dye having the formula

31

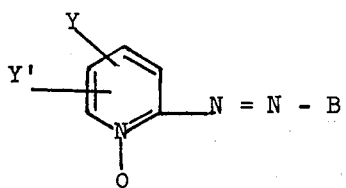

2. a dye having the formula

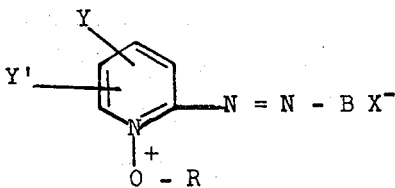

and mixtures thereof, wherein
Y and Y' each independently represent a member selected from the group consisting of hydrogen, halogen, nitro and lower alkyl having 1–4 carbon atoms;
R represents lower alkyl having 1–4 carbon atoms;
X⁻ represents an anion, said anion being perchlorate or alkylsulfate;
B represents a member selected from the group consisting of
a. phenyl substituted in a position selected from the group consisting of ortho and para positions relative to the nitrogen atom of the disazo link, by a member selected from the group consisting of hydroxy, primary amino, tertiary amino and mixtures thereof, said substituted phenyl (1) being optionally further substituted by a substituent selected from the group consisting of lower alkyl having 1–4 carbon atoms, lower alkoxy having 1–4 carbon atoms, halogen, primary amino, tertiary amino, acetamido, nitro, hydroxy and mixtures thereof or (2) being condensed with benzene, pyridine or morpholine ring; and
b. a group of the formula

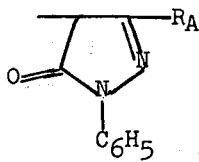

wherein
$R_A$ is selected from the group consisting of methyl and ethyl and at least one other direct hair dye, said other direct hair dye being an indamine, indoaniline, indophenol, anthraquinone, nitrobenzene, or an azo dye other than that previously defined, said composition having a pH ranging from 3–9.5.

2. A dye composition for human hair comprising a solution in a solvent selected from the group consisting of water and a hydroalcoholic solution wherein said hydroalcoholic solution is an aqueous solution of a lower aliphatic alcohol of 1 to 4 carbon atoms and about 0.001–1 percent by weight of at least one dye selected from the group consisting of
1. a dye having the formula

32

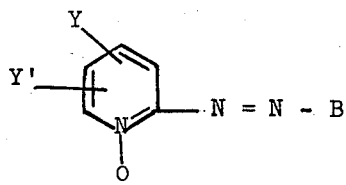

2. a dye having the formula

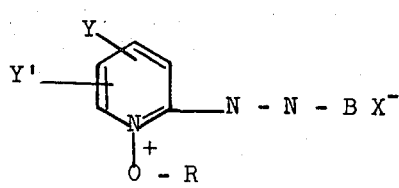

and mixtures thereof, wherein
Y and Y' each independently represent a member selected from the group consisting of hydrogen, halogen, nitro and lower alkyl having 1–4 carbon atoms;
R represents lower alkyl having 1–4 carbon atoms;
X⁻ represents an anion, said anion being perchlorate or alkylsulfate;
B represents a member seected from the group consisting of
a. phenyl substituted in a position selected from the group consisting of ortho and para positions relative to the nitrogen atom of the disazo link, by a member selected from the group consisting of hydroxy, primary amino, tertiary amino and mixtures thereof, said substituted phenyl (1) being optionally further substituted by a substituent selected from the group consisting of lower alkyl having 1–4 carbon atoms, lower alkoxy having 1–4 carbon atoms, halogen, primary amino, tertiary amino, acetamido, nitro, hydroxy and mixtures thereof or (2) being condensed with benzene, pyridine or morpholine ring; and
b. a group of the formula

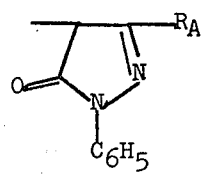

wherein
$R_A$ is selected from the group consisting of methyl and ethyl and a cosmetic film-forming resin in an amount of 1–3 percent by weight of said composition and wherein said alcohol is present in an amount of about 20–70 percent by weight of said composition wherein said cosmetic film-forming resin is selected from the group consisting of polyvinylpyrrolidone, a copolymer of vinyl acetate and crotonic acid, and a copolymer of vinylpyrrolidone and vinyl acetate, said composition having a pH ranging from 3–9.5

3. A process for dyeing human hair comprising

A. applying to said hair in an amount effective to dye said hair a dye composition comprising a solution in a solvent selected from the group consisting of water and a hydroalcoholic solution of about 0.001–1 percent by weight of at least one dye selected from the group consisting of
1. a dye having the formula

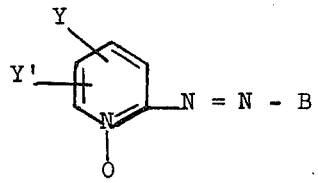

and
2. a dye having the formula

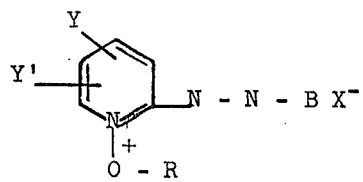

and mixtures thereof, wherein

Y and Y' each independently represent a member selected from the group consisting of hydrogen, halogen, nitro and lower alkyl having 1–4 carbon atoms;

R represents lower alkyl having 1–4 carbon atoms;

$X^-$ represents an anion, said anion being perchlorate or alkylsulfate;

B represents a member selected from the group consisting of
  a. phenyl substituted in a position selected from the group consisting of ortho and para positions relative to the nitrogen atom of the disazo link, by a member selected from the group consisting of hydroxy, primary amino, tertiary amino and mixtures thereof, said substituted phenyl (1) being optionally further substituted by a substituent selected from the group consisting of lower alkyl having 1–4 carbon atoms, lower alkoxy having 1–4 carbon atoms, halogen, primary amino, tertiary amino, acetamido, nitro, hydroxy and mixtures thereof or (2) being condensed with benzene, pyridine or morpholine ring; and
  b. a group of the formula

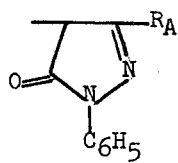

wherein $R_A$ is selected from the group consisting of methyl and ethyl, said composition having a pH ranging from 3–9.5;

B. permitting said composition to remain in contact with said hair for a period ranging between about 3–40 minutes, C. rinsing, washing and drying said hair.

4. A process for dyeing human hair comprising
A. applying to previously washed and rinsed hair in an amount effective to dye said hair, a composition comprising a solution in a solvent, said solvent being a lower aliphatic alcohol containing 1–4 carbon atoms in an amount of 20–70 percent by weight of said composition; 0.001–1 percent by weight of at least one dye selected from the group consisting of
1. a dye having the formula

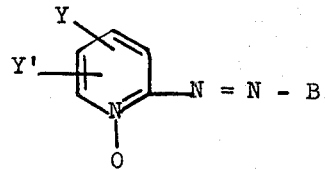

and
2. a dye having the formula

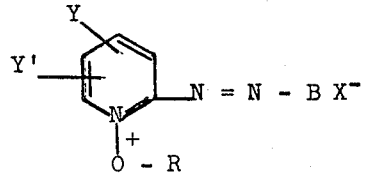

and mixtures thereof, wherein

Y and Y' each independently represent a member selected from the group consisting of hydrogen, halogen, nitro and lower alkyl having 1–4 carbon atoms;

R represents lower alkyl having 1–4 carbon atoms;

$X^-$ represents an anion, said anion being perchlorate or alkylsulfate;

B represents a member selected from the group consisting of
  a. phenyl substituted in a position selected from the group consisting of ortho and para positions relative to the nitrogen atom of the disazo link, by a member selected from the group consisting of hydroxy, primary amino, tertiary amino and mixtures thereof, said substituted phenyl (1) being optionally further substituted by a substituent selected from the group consisting of lower alkyl having 1–4 carbon atoms, lower alkoxy having 1–4 carbon atoms, halogen, primary amino, tertiary amino, acetamido, nitro, hydroxyl and mixtures thereof or (2) being condensed with benzene, pyridine or morpholine ring; and
  b. a group of the formula

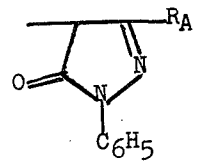

wherein $R_A$ is selected from the group consisting of methyl and ethyl, said composition having a pH ranging from 3–9.5; and also includes cosmetic film-forming resin in an amount of 1–3 percent by weight of said composition wherein said cosmetic film-forming resin is selected from the group consisting of polyvinylpyrrolidone, a copolymer of vinyl acetate and crotonic acid, and a copolymer of vinylpyrrolidone and vinyl acetate;

B. rolling said hair up on curlers and drying said hair.

* * * * *

UNITED STATES PATENT OFFICE
CERTIFICATE OF CORRECTION

Patent No. 3,955,918     Dated May 11, 1976

Inventor(s) Gerard Lang

It is certified that error appears in the above-identified patent and that said Letters Patent are hereby corrected as shown below:

In the Heading

The foreign application priority data should read:

June 19, 1972    Luxemburg 65,539--

Signed and Sealed this

Twenty-sixth Day of April 1977

[SEAL]

Attest:

RUTH C. MASON
Attesting Officer

C. MARSHALL DANN
Commissioner of Patents and Trademarks